United States Patent [19]

Teranishi et al.

[11] Patent Number: 4,472,377
[45] Date of Patent: Sep. 18, 1984

[54] METHOD AND COMPOSITION FOR LURING COYOTES

[75] Inventors: Roy Teranishi, Albany; Walter E. Howard, Davis, both of Calif.

[73] Assignee: The United States of America as represented by the Secretary of Agriculture, Washington, D.C.

[21] Appl. No.: 288,261

[22] Filed: Jul. 29, 1981

[51] Int. Cl.³ .............................. A01N 25/00
[52] U.S. Cl. ........................................ 424/84
[58] Field of Search .......................... 424/84

[56] References Cited

FOREIGN PATENT DOCUMENTS 1028930 3/1965 United Kingdom ............. 260/501.1

OTHER PUBLICATIONS

Bullard et al. I, Preparation and Evaluation of a Synthetic Fermented Egg Coyote Attractant and Deer Repellent, J. Agric. Food Chem., vol. 26, No. 1, 1978.
Timm et al., Coyotes Respond to Fractions of Coyote Urine, Science of Biology Journal, vol. 1, No. 3, Jul. 1975.
Bullard et al. II, Volatile Components of Fermented Egg, An Animal Attractant and Repellent, J. Agric. Food Chem., vol. 26, No. 1, 1978.
E. L. Murphy et al., Flavor Chemistry of Animal Foods, American Chemical Society Symposium Series, No. 67, Ed. by Roger W. Bullard, ACS, Washington, (1978), pp. 66–77.

Primary Examiner—Jerome D. Goldberg
Assistant Examiner—John M. Kilcoyne
Attorney, Agent, or Firm—M. Howard Silverstein; David G. McConnell; Margaret A. Connor

[57] ABSTRACT

The method and composition of the invention comprises one or more synthetically prepared, substantially pure compounds effective as odor attractants to lure coyotes having the structure—

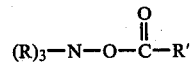

where R is hydrogen or methyl and R' is hydrogen, secondary butyl or alkyl containing 1 to 17 carbon atoms placed on a solid substrate in an amount sufficient to attract coyotes.

20 Claims, 4 Drawing Figures

METHOD AND COMPOSITION FOR LURING COYOTES

FIELD OF THE INVENTION

This invention relates to and has among its objects the provision for using odor attractants to lure coyotes.

DESCRIPTION OF THE PRIOR ART

Most of the sheep killed by predation in the United States are killed by coyotes. The greatest problem of using a trap or chemical agent to affect coyote populations is to attract the coyote (E. L. Murphy et al., *Flavor Chemistry of Animal Foods*, American Chemical Society Symposium Series, No. 67, Ed. by Roger W. Bullard, ACS, Washington (1978), pp. 66–77). Scent baits to lure coyotes into the vicinity of a device to kill or trap them have consisted of empirical mixtures of food, animal organs, blood, urine and the like brewed and/or fermented for weeks and months (Murphy et al.). A trapper or animal damage control agent has his own favorite lure formula. Since no formula is standard, there is significant variation in the degree of success as an attractant and amounts to be used can not be quantified. Furthermore, the degree of specificity of attracting coyotes varies.

SUMMARY OF THE INVENTION

The invention described herein provides a means for obviating the above problems. The method and composition of the invention comprises one more synthetically prepared, substantially pure compounds effective as odor attractants to lure coyotes having the structure—

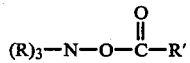

where R is hydrogen or methyl and R' is hydrogen, secondary butyl or alkyl containing 1 to 17 carbon atoms placed on a solid substrate in an amount sufficient to attract coyotes.

One advantage of the invention is that the compounds can be readily synthetically prepared in a substantially pure form and quantitated amounts used to attract coyotes to maximize the degree of success of the attractants.

Another advantage of the invention is the compounds not only attract coyotes to the control agents or traps but produce a licking, chewing and biting response. This is essential where control of the coyote is by ingestion of toxicants, antifertility agents, tranquilizers and the like. In cases where the toxicant or control agent is by forced ingestion, such as when using a cyanide gun, the lick-chew response produced by the compounds of the invention is essential to trigger the cyanide gun.

Another advantage of the invention is that the compounds which evoke a specific response such as coyote sniffing or licking and chewing can be used alone or mixed with another compound of the invention having a response quantitatively different to thereby tailor coyote response to the coyote-control device used. Since the amount of compound used can be quantitated, the variation in the degree of success of the attractant can be minimized.

Another advantage is that the compounds of the invention release ammonia, trimethylamine and organic acids, which are found in coyote urine and are associated with sex, thus, it is unlikely that the coyotes, though very adaptive, would readily adapt away from lures containing compounds of the invention. Since only carnivores are attracted to the compounds, sheep, cows, deer, rabbits and the like would not be inadvertently attracted to and harmed by control agents or traps.

Another advantage is that the compounds of the invention can be used alone, or as the basis for formulating coyote attractants using other additives such as taste attractants, antifertility agents and the like. Furthermore, the compounds can be added to a commerical lure formulation to enhance or intensify the coyote attractant response and/or licking and chewing response of the lure.

The compounds of the invention can be readily prepared from readily available, inexpensive and stable materials. Furthermore, treatment with the effective attractants reduces the number of lures required and thus reduces the cost and labor involved.

DETAILED DESCRIPTION OF THE INVENTION

Figure 1:
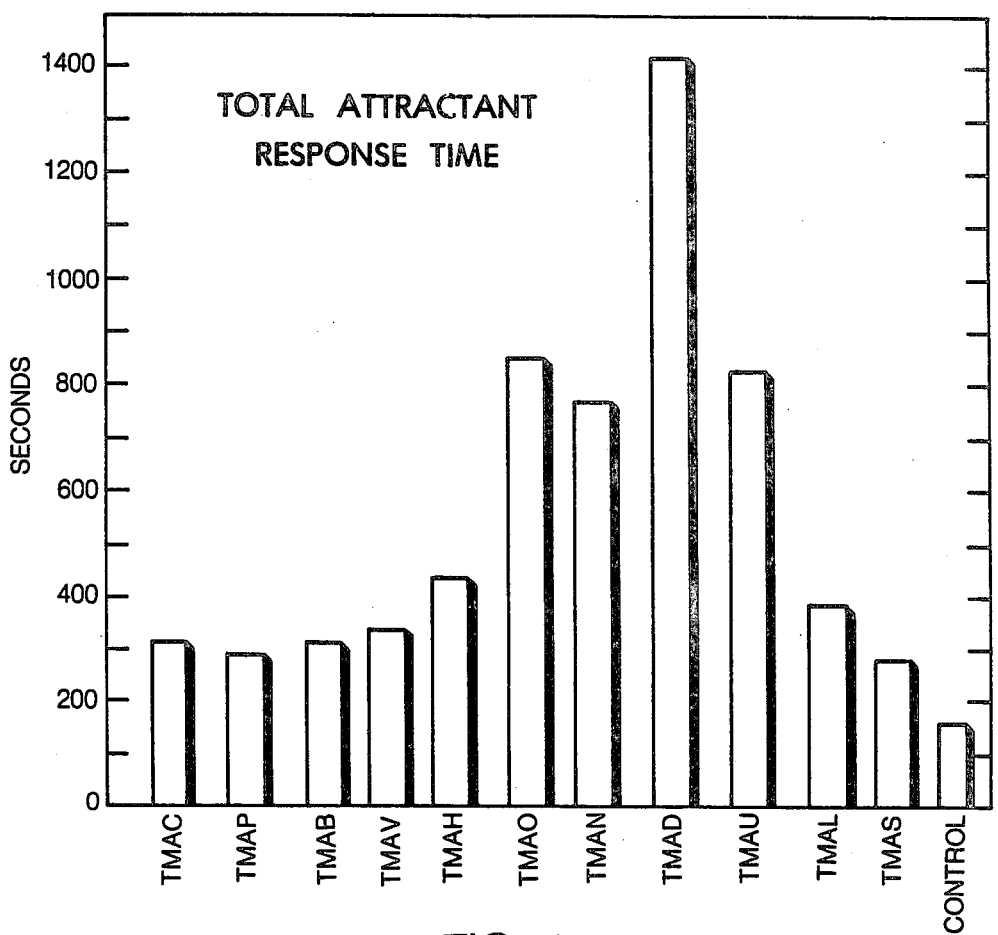
FIG. 1 shows coyote attractant response to compounds of the invention.

The method and composition of the invention comprises a solid substrate having placed thereon one or more synthetically prepared, substantially pure compounds effective as odor attractants to lure coyotes having the structure—

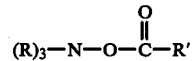

wherein R is hydrogen or methyl and R' is hydrogen, secondary butyl or alkyl containing 1 to 17 carbon atoms, in an amount sufficient to attract coyotes.

The compounds of the invention (odor attractants) may be used alone or diluted as required for ease of application. The amount used should be that sufficient to attract coyotes. In an alternate embodiment of the invention, one or more of the compounds of the invention are added to lard, animal organs, urine or other known bait lure to enhance the attractancy effect of the lures.

Where the compounds of the invention are used alone, an amount sufficient to at least 1 microliter is used. Where the odor attractant compounds are diluted with lard or other bait lure, at least 1 ppm of attractant is added to the diluent lure. One formulation used to attract coyotes is 0.05 ml of attractant to 3.8 liters of bait.

The solid substrate comprises a fencepost, bait post as described by Teranishi et al. in patent application Ser. No. 288259 filed of even date, tree, or the ground. In an alternate embodiment, the solid substrate is a pliable porous material such as a sheepskin, rabbit skin, heavy fabric, heavy plastic, and the like. The latter, after addition of the odor attractants of the invention, are then placed on the ground, bait post or the like. In all cases, the solid substrate should at least partially absorb or adsorb the compounds of the invention so that they are released over a period of time sufficient to attract coyotes, that is, at least a day and preferably a week or more.

In the method of the invention, the odor attractant is placed on the solid substrate and the latter is placed in the vicinity of control devices such as traps or cyanide guns. In an alternate embodiment, control agents such as toxicants, tranquilizers, antifertility agents and the like are placed on the solid substrate along with the odor attractant so that when the coyote licks and chews the substrate, the control agents are ingested and the coyote controlled.

As stated previously, the compounds of the invention are synthetically produced, substantially pure compounds.

Preparation of the compounds is as follows:

A. Trimethylammonium salts: Trimethylamine (TMA), cooled to below the boiling point of 2° C. and preferably to at least −10° C. is added to an acid of the formula—

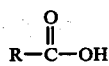

wherein R is hydrogen, secondary butyl or alkyl containing 1 to 17 carbon atoms. The reaction is carried out at 0° C. Sufficient excess TMA to organic acid, based on an equivalent basis, is used, to ensure substantially complete reaction. The excess TMA is allowed to evaporate off leaving the substantially pure salt.

B. Ammonium salts are prepared by bubbling excess anhydrous ammonia into the organic acid at 0° C. The excess ammonia is allowed to evaporate so as to obtain a substantially pure salt.

The invention is further demonstrated by the following illustrative examples.

EXAMPLE 1

1000 g (5.8 moles) of decanoic acid is warmed above its melting point and transferred to a reaction vessel having a dry ice finger-type condenser. 600 g (10 moles) of TMA, cooled to −10° C. in a salt-ice mixture, is poured into the reaction vessel at 0° C. The mixture is maintained at 0° C. After formation of the salt, excess TMA is allowed to evaporate at room temperature leaving trimethylammonium decanoate (TMAD).

EXAMPLE 2

Into a reaction vessel containing 1000 g (6.9 moles) of octanoic acid at 0° C. is bubbled anhydrous ammonia at a rate of 10 g per minute for 20 minutes (11.8 moles). The reaction is carried out at 0° C. Excess ammonia is allowed to evaporate leaving ammonium octanoate.

The compounds were evaluated as coyote scent baits as described in "A Method of Evaluating Coyote Scent Baits" by R. M. Timm et al., in *Test Methods for Vertebrate Pest Control and Management Materials*, ASTM STP 625, Ed. by W. B. Jackson and R. E. Marsh, American Society for Testing Materials, Philadelphia, Pa. (1977), pp. 151–156. Briefly stated, the procedure involves the release of individual adult coyotes into a test area for a set period. Immediately preceding release of each coyote into the test area, 0.5 ml of the test compound is placed on adsorbent cotton and mounted between perforated discs secured between two metal plates or on sheepskins placed on scent posts. Responses are observed and recorded.

Figure 2:
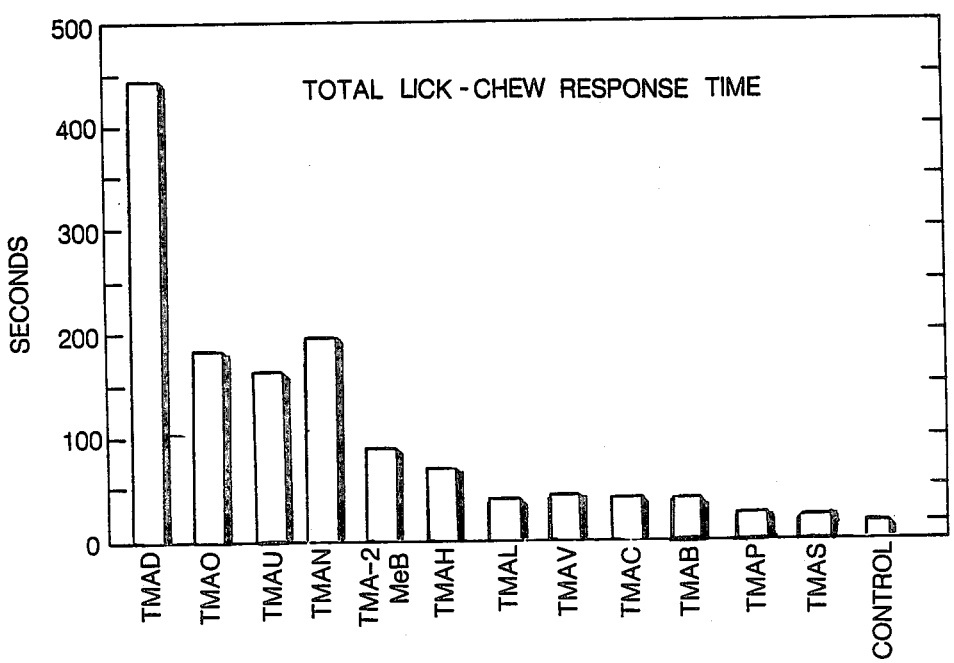
FIG. 2 shows coyote lick-chew response to compounds of the invention.

FIGS. 1 and 2 show the responses of coyotes to trimethylammonium salts of the carbonic acid (TMAC), propanoic acid (TMAP), butyric acid (TMAB), valeric acid (TMAV), hexanoic acid (TMAH), octanoic acid (TMAO), nonanoic acid (TMAN), decanoic acid (TMAD), undecanoic acid (TMAV), lauryl acid (TMAL) and stearic acid (TMAS). The control was a scent station with no odorant. The amount of each compound used was 0.5 ml. The total time spent by 10 test animals at the scent stations was measured. Test animals were observed individually two times.

As shown in FIG. 1 all the compounds tested attracted the coyotes more than the control. Trimethylammonium decanoate (TMAD) evoked the most response. The coyotes spent a total of 1413 seconds at the bait station having TMAD vs 167 seconds at the conrol station. TMAO, TMAU and TMAN also showed attention holding ability of 852, 827, and 771 seconds, respectively. In addition to attracting the coyotes attention to a bait, it is important that the odor attractant hold the animal's attention for a period of time because the coyote must ingest the bait for effective use of the bait.

FIG. 2 depicts the total time spent by the coyotes licking or chewing the sheepskin or fabric upon which the compounds were placed. Also included in this test was the trimethylammonium salt of 2-methylbutyric acid (TMA-2 MeB). Again, all of the compounds of the invention tested showed a greater lick-chew response than the control. TMAD showed the greatest response of 443 seconds vs the control of 20 seconds.

The following illustrates the use of a compound of the invention with coyote bait lures. This is by way of illustration, and not limitation.

TMAD was added to standard baits (coyote urine, organs and brains) in a concentration of 0.2 to 1.0 ml TMAD to 946 ml of bait. The baits were placed on 108 traps and 35 cyanide gun control devices. Ninety-eight coyotes were trapped and 27 taken with cyanide guns.

In an alternate embodiment of the invention, one or more compounds which enhance the odor attractancy effect of the compounds of the invention are added thereto. Such additives are include:

A. Sulfides having the general formula—

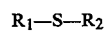

wherein $R_1$ is methyl or ethyl and $R_2$ is alkyl having 1–5 carbon atoms or isopentenyl. Compounds of this formula particularly suitable are ethyl butyl sulfide (ESB), methyl propyl sulfide and methyl isopentenyl sulfide.

B. Disulfides of the formula—

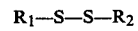

wherein $R_1$ and $R_2$ are alkyl containing 1–4 carbon atoms. N-butyl disulfide is particularly suitable.

C. Methyl ketones of the formula—

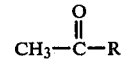

where R is alkyl having 7–9 carbon atoms.

D. Diamino compounds having the general formula—

$$NH_2(CH_2)_n-NH_2$$

where n is 4–5.

E. Putrescine and cadaverine

The above additives are added in at 0.1 to 15 percent (w/w) with respect to compounds of the invention. They are either mixed with the odor attractant compounds and applied to the solid substrate or applied separately from the compounds of the invention to the substrate.

Figure 3:
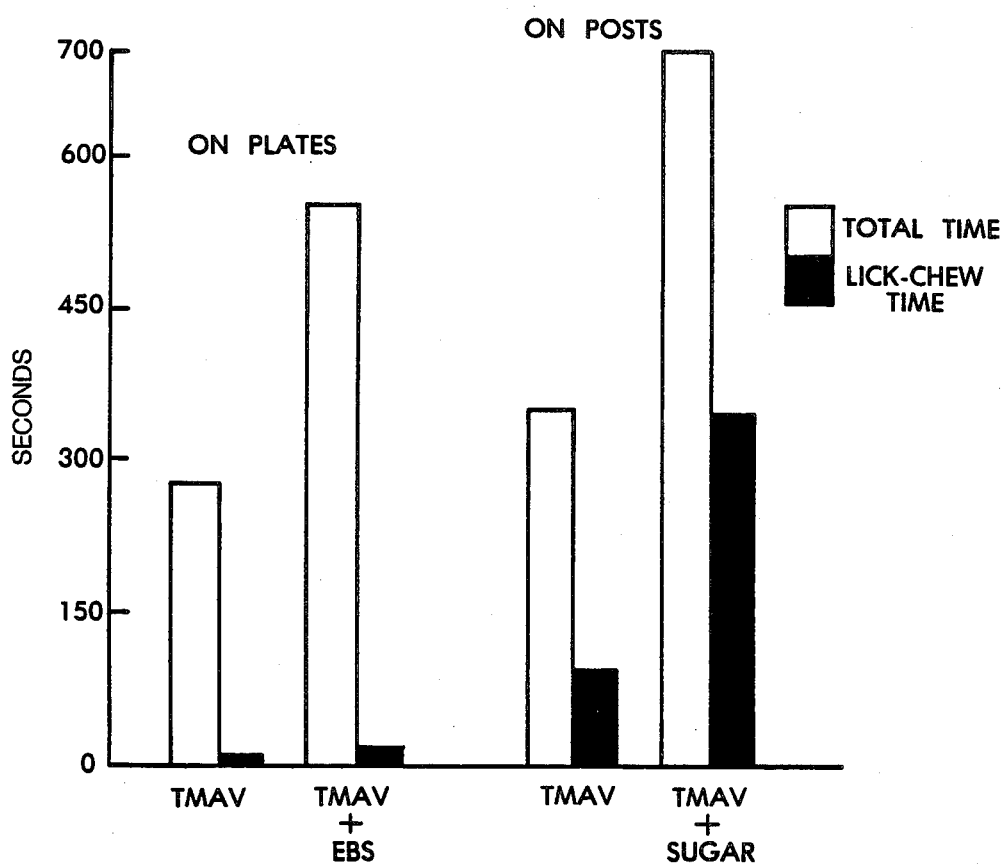
FIGS. 3 and 4 show coyote response to compounds of the invention containing additives to enhance the response.

FIG. 3 shows the increase in attractancy to coyotes of trimethylammonium valerate (TMAV) after the addition of ethyl butyl sulfide (ESB) (10% ESB/TMAV, w/w). The responses measured were: (a) the total attractant response time and (b) the licking and chewing time of ten coyotes during a 10-minute exposure to scent plates. Both responses doubled when ESB was added.

Figure 4:
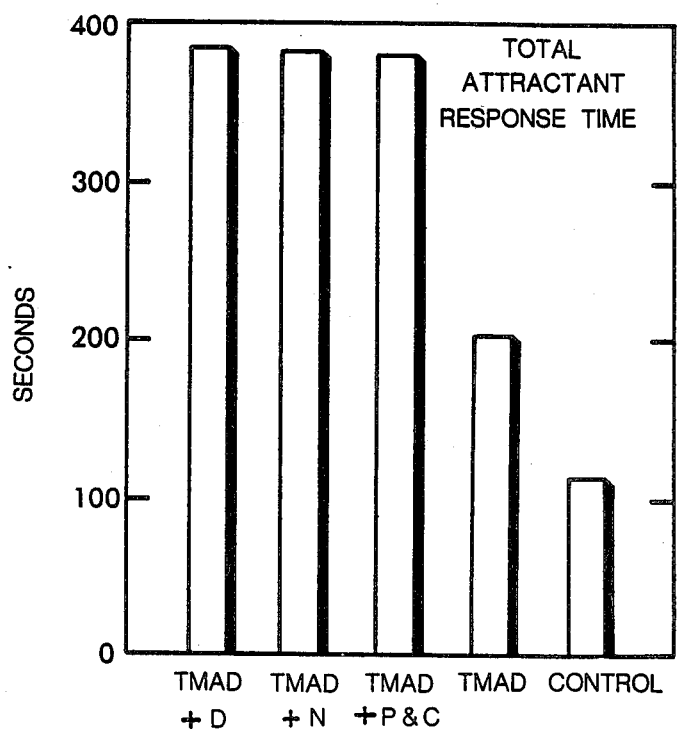

FIG. 4 shows the increase in attractancy of trimethylammonium decanoate (TMAD) to coyotes upon the addition of the methyl ketones 2-decanone (D) and 2-nonanone (N). The amount used was 10% ketone to TMAD (w/w). The control is a scent station with no odorant. The total attractant response time of ten coyotes during individual 10-minute exposures was measured. The addition of the methyl ketones to TMAD nearly doubled the time the coyotes spent at the bait station having TMAD alone and nearly quadrupled the time spent at the control.

FIG. 4 also shows the use of the chemical compounds putrescene (P) and cadaverine (C), found as breakdown products of decaying meat, to enhance the attractancy of coyotes to scent posts scented with trimethylammonium decanoate (TMAD). P and C were added in an amount of 10% total P and C to TMAD. The response time for 10 coyotes was measured during 10 minute exposures. The addition of P and C nearly doubled the time the coyotes spent at scent stations over those having TMAD alone.

In another embodiment of the invention, sucrose is added to the invention to enhance the licking and biting response of coyotes at bait posts (FIG. 3). A sheepskin having a compound of the invention placed thereon is dipped in a sucrose solution prior to placing on the ground or bait post. This embodiment has the further advantage of making the control compounds more selective because felids (bobcats, cougars, domestic cats, and the like) do not respond to sweet compounds whereas coyotes (canids) do (J. C. Boudreau and T. D. White, "Flavor Chemistry of Carnivore Taste Systems, In *Flavor Chemistry of Animal Foods,* American Chemical Society Symposium Series, No. 67, ACS, Washington (1978), pp. 102–128).

Having thus described the invention, what is claimed is:

1. A composition, useful in luring coyotes, comprising:
a synthetically produced, substantially pure compound of the structure—

$$(R)_3-N-O-\overset{O}{\overset{\|}{C}}-R'$$

wherein R is hydrogen or methyl and R' is hydrogen, secondary butyl or straight chain alkyl containing 1 to 17 carbon atoms, in an amount sufficient to lure coyotes,
and a solid substrate which at least partially adsorbs said compound.

2. The composition of claim 1 wherein the amount of said pure compound is at least 1 microliter.

3. The composition of claim 1 wherein said solid substrate is a sheepskin.

4. The composition of claim 1 also containing a coyote bait lure.

5. The composition of claim 4, wherein the amount of said compound added to said coyote bait lure is at least 1 ppm.

6. The composition of claim 1 which also contains an additive of the structure—

$$R_1-S-R_2$$

wherein $R_1$ is methyl or ethyl and $R_2$ is an alkyl having 1–5 carbon atoms or isopentenyl, in an amount of about 0.1 to 15 percent (weight/weight) with respect to said compound.

7. The composition of claim 6 wherein said additive is ethyl butyl sulfide.

8. The composition of claim 1 which also contains an additive of the structure—

$$R_1-S-S-R_2$$

wherein $R_1$ and $R_2$ are alkyl containing 1–4 carbon atoms, in an amount of about 0.1 to 15 percent (weight/weight) with respect to said compound.

9. The composition of claim 8 wherein said additive is N-butyl disulfide.

10. The composition of claim 1 which also contains an additive of the structure—

$$CH_3-\overset{O}{\overset{\|}{C}}-R$$

wherein R is alkyl having 7–9 carbon atoms, in an amount of about 0.1 to 15 percent (weight/weight) with respect to said compound.

11. The composition of claim 10 wherein said additive is 2-decanone.

12. The composition of claim 10 wherein said additive is 2-nonanone.

13. The composition of claim 1 which also contains a mixture of putrescine and cadaverine in an amount of about 0.1 to 15 percent (weight/weight) with respect to said compound.

14. A coyote lure of the type which contains animal blood, brains, urine or other bait lure, which also contains an amount sufficient to lure coyotes of a synthetically produced, substantially pure compound of the structure—

$$(R)_3-N-O-\overset{O}{\overset{\|}{C}}-R'$$

wherein R is hydrogen or methyl and R' is hydrogen, secondary butyl or straight chain alkyl containing 1 to 17 carbon atoms.

15. A method for luring coyotes, comprising: applying a synthetically produced, substantially pure compound of the structure—

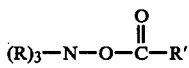

wherein R is hydrogen or methyl and R' is hydrogen, secondary butyl or straight chain alkyl containing 1 to 17 carbon atoms, to a solid substrate which at least partially adsorbs said compound, in an amount sufficient to lure coyotes, and placing the solid substrate in the locus of coyotes.

16. The method of claim 15 wherein said compound is mixed with an additive of the structure—

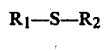

wherein $R_1$ is methyl or ethyl and $R_2$ is alkyl having 1–5 carbon atoms or isopentenyl, said amount of additive being about 0.1 to 15 percent (weight/weight) with respect to said compound.

17. The method of claim 15 wherein said compound is mixed together with in additive of the structure—

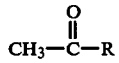

wherein R is alkyl having 7–9 carbon atoms, said amount of additive being about 0.1 to 15 percent (weight/weight) with respect to said compound.

18. The method of claim 15 wherein said compound is mixed together with a mixture of putrescine and cadaverine, said mixture being about 0.1 to 15 percent (weight/weight) with respect to said compound.

19. The composition of claim 1 wherein said synthetically produced, substantially pure compound is trimethylammonium decanoate.

20. A method for luring coyotes comprising applying to the locus of coyotes an amount sufficient to lure coyotes of a synthetically produced, substantially pure compound of the structure

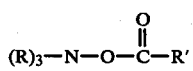

wherein R is hydrogen or methyl and R' is hydrogen, secondary butyl or straight chain alkyl containing 1 to 17 carbon atoms.